(12) United States Patent
Takano et al.

(10) Patent No.: US 8,064,648 B2
(45) Date of Patent: Nov. 22, 2011

(54) EYE FORM CLASSIFYING METHOD, FORM CLASSIFICATION MAP, AND EYE COSMETIC TREATMENT METHOD

(75) Inventors: Ruriko Takano, Tokyo (JP); Etsu Nishijima, Tokyo (JP); Hiroshi Tanaka, Tokyo (JP); Tamae Okano, Tokyo (JP); Momoe Futagi, Tokyo (JP); Minako Nakamura, Tokyo (JP)

(73) Assignee: Shiseido Co., Ltd., Chuo-ku, Toyko (JP)

( * ) Notice: Subject to any disclaimer, the term of this patent is extended or adjusted under 35 U.S.C. 154(b) by 552 days.

(21) Appl. No.: 12/203,465

(22) Filed: Sep. 3, 2008

(65) Prior Publication Data

US 2009/0000637 A1 Jan. 1, 2009

Related U.S. Application Data

(62) Division of application No. 10/562,420, filed as application No. PCT/JP2004/009155 on Jun. 29, 2004, now Pat. No. 7,436,987.

(30) Foreign Application Priority Data

Jun. 30, 2003 (JP) .................................. 2003-188774
Oct. 30, 2003 (JP) .................................. 2003-371235

(51) Int. Cl.
*G06K 9/00* (2006.01)
*G09B 23/28* (2006.01)
(52) U.S. Cl. ........................................ 382/117; 434/271
(58) Field of Classification Search .................. 382/117; 434/271
See application file for complete search history.

(56) References Cited

U.S. PATENT DOCUMENTS

| 4,045,883 A | * | 9/1977 | Ryan .............................. 434/155 |
| 5,432,866 A | | 7/1995 | Sakamoto |
| 5,495,338 A | * | 2/1996 | Gouriou et al. ................ 356/402 |
| 5,520,203 A | | 5/1996 | Segerstrom |
| 5,867,588 A | | 2/1999 | Marquardt |

(Continued)

FOREIGN PATENT DOCUMENTS

EP 0828230 3/1998

(Continued)

OTHER PUBLICATIONS

Japanese Patent Abstract Publication No. 10289303, published Oct. 27, 1998, one page.

(Continued)

*Primary Examiner* — John Strege
(74) *Attorney, Agent, or Firm* — Rankin, Hill & Clark LLP

(57) ABSTRACT

A classifying method according to an eye form considers the eye form feature as an important factor, to provide an eye cosmetic treatment method for appropriately and quickly making up the eye so that the eye balances and looks large and attractive according to the type categorized by the classifying method. A makeup tool is devised by integrating an eye form feature analyzing method with a form shaping method by markup. An eye form classifying method uses as indexes, three forms, namely, the eye frame form showing the shape of the eye contour, the eye form showing the three-dimensional shape of the eye, and the angle form of the inner corner and outer edge, the eye forms are classified. The eye forms are classified by comparing the eye form with the eye form of a reference balanced eye.

2 Claims, 14 Drawing Sheets

U.S. PATENT DOCUMENTS

| | | | |
|---|---|---|---|
| 5,971,763 A | | 10/1999 | Yau |
| 6,091,836 A * | | 7/2000 | Takano et al. .................. 382/118 |
| 6,937,755 B2 * | | 8/2005 | Orpaz et al. .................. 382/162 |
| 7,079,158 B2 * | | 7/2006 | Lambertsen .................. 345/630 |
| 7,123,753 B2 * | | 10/2006 | Takahashi et al. ............ 382/117 |
| 7,146,983 B1 | | 12/2006 | Hohla et al. |
| 2003/0053663 A1 | | 3/2003 | Chen et al. |
| 2003/0149347 A1 | | 8/2003 | Kauffmann et al. |

FOREIGN PATENT DOCUMENTS

| | | |
|---|---|---|
| JP | 60-122107 | 8/1985 |
| JP | 10-289322 | 10/1998 |
| JP | 2000-14661 | 1/2000 |
| JP | 2001-148018 | 5/2001 |
| JP | 2002-123585 | 4/2002 |
| JP | 10-289303 | 2/2009 |

OTHER PUBLICATIONS

Supplementary European search report for PCT/JP2004/009155 mailed Mar. 20, 2008, 5 pages.

European Examination Report for EP 04746624.8 dated Jan. 26, 2009, five pages.

Japanese Patent Abstract Publication No. 2001-148018 published May 29, 2001, one page.

Japanese Patent Abstract Publication No. 2002-123585 published Apr. 26, 2002, one pge.

International Search Report for Application No. PCT/JP2004/009155, 2 pages, Oct. 12, 2004.

* cited by examiner

FRAME OF TARGET EYE

FRAME OF REFERENCE BALANCE EYE

SUPERIMPOSING WITH REFERENCE BALANCE EYE BY SUPERIMPOSING BLACK EYES

ONLY MASCARA IS HEAVILY APPLIED TO THE UPPER AND LOWER LASHES.

EXTEND THE EYE LINE ALONG THE LASH LINE, AND SMUDGE IT AWAY. PLACE SHADOW ON THE UPPER LID TO ADD DEPTH. THEN, ADD THE FALSE EYELASH ONTO THE UPPER LASH.

BEFORE MAKEUP

HIGHLIGHT THE EYELASH LINE WITH BLACK EYELINER, AND OUTLINE THE FRAME. THEN, SMUDGE THE EXTENDED UPPER EYE LINE ONLY.

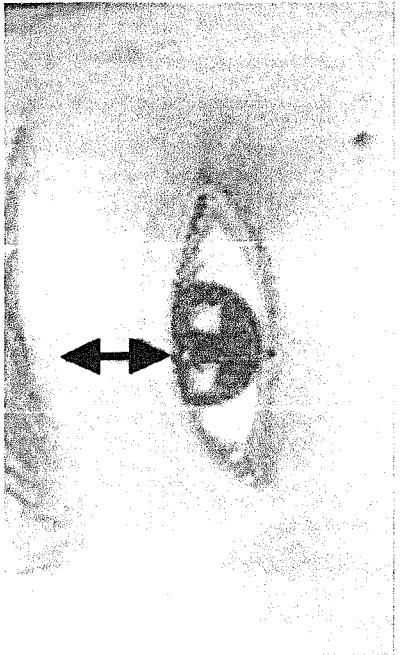
FIG.10B SURROUNDING A FRAME
FIG.10A AN EYE OF MODEL A
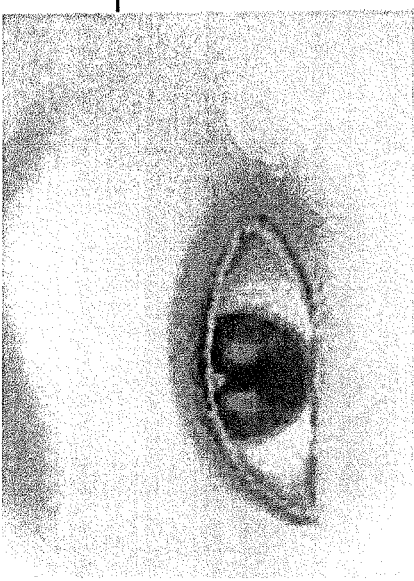
FIG.10C COMPARING A STANDARD EYE FRAME
VERTICAL WIDTH IS NARROW
WIDTH IS WIDE
UPWARD SLANTING EYES BEFORE MAKEUP
AFTER MAKEUP
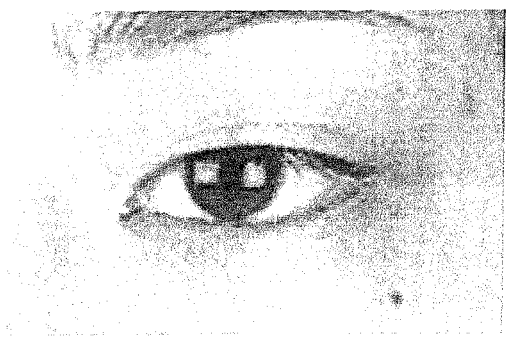
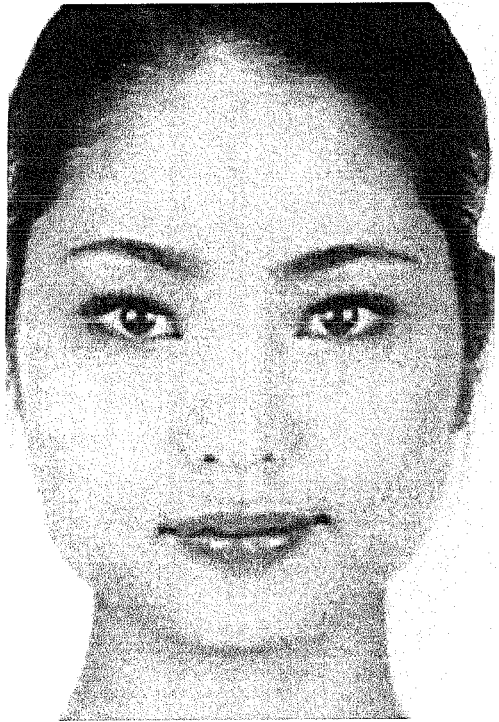
FIG.12A
FIG.12B

EYE FORM CLASSIFYING METHOD, FORM CLASSIFICATION MAP, AND EYE COSMETIC TREATMENT METHOD This application is a division of U.S. application Ser. No. 10/562,420, filed Dec. 27, 2005, now U.S. Pat. No. 7,436,987, which is a national stage entry of PCT/JP2004/009155, with an international filing date of Jun. 29, 2004, which claims foreign priority to 2003-188774 filed Jun. 30, 2003 and further claims foreign priority to 2003-371235 filed Oct. 30, 2003.

TECHNICAL FIELD

The present invention relates to a method for classifying eyes based on a form thereof, to an eye form map for collectively presenting the classified eyes, and to an eye cosmetic treatment method to be applied according to the eye form, so as to be able to bring an eye closer to a standard balanced eye.

BACKGROUND ART

In recent years, interest in an eye makeup method, i.e., an eye cosmetic treatment method, has been growing, and information on cosmetic treatment methods, cosmetic items, and makeup tools is introduced in a variety of beauty magazines or general magazines, and the like. However, the conventionally proposed eye makeup methods are not designed to extract only eyes and apply makeup only to eyes while understanding eye features. Instead, they simply pay attention to eyes in terms of a balance with an entire face. Such a cosmetic treatment method that pays attention to eyes in entire face is disclosed in, for instance, Japanese Patent Application Laid-Open No. 10-289322, and Japanese Patent Application Laid-Open No. 2000-14661.

Although it is a vital factor in achieving an effect of makeup, and many are longing to have eyes having the form features of being large and bright, the information viewed from the aspect of eye forms is extremely little available. Eye features such as single-edged eyelid, double-edged eyelid, downward slanting eyes, and the like are roughly identified, these features being extracted as negative features, and makeup methods for adjusting them are simply presented case by case.

Classifying eyes based on the form features is imperative in understanding eye features of individual persons and in deciding a makeup treatment according to the features. As the situation stands now, however, no method of picking up more detailed elements and systematically classifying them has been presented although there is some classification of upper lids that is designed to describe racial features in anthropology. Furthermore, no classification of the eye form features that could be associated with eye makeup methods has been proposed. Moreover, with makeup methods on case-by-case basis, it would be difficult to find a way to make individually different eyes look attractive. In fact, trying and failing, the methods simply give eye makeup adapted to individual persons who fix their faces, which is an inefficient process of trial and error. In terms of improvement of techniques of beauty technicians, as neither systematized analyzing method nor makeup method is available, experience is an indispensable factor.

DISCLOSURE OF THE INVENTION

The present invention has the task of presenting a classification method according to the eye form type considering the eye form feature as the indispensable factor, providing an eye cosmetic treatment method for appropriately and quickly making up the eye so that the eye looks balanced, large and attractive according to the type categorized by the classification method, and providing a makeup tool devised by integrating an eye form feature analyzing method with a form shaping method by makeup.

The means the present invention has adopted to solve the above problems is characterized by an eye form classification method in which the eye forms are classified by using three forms as indexes, namely, the eye frame form showing the shape of the eye contour, the eye form showing the three-dimensional shape of the eye, and the angle form of the inner corner and outer edge. The present invention is also characterized in that the eye forms are classified by comparing the eye form with the standard balanced eye form. The three-dimensional shape of the eye grasps, for example, eyelid grooves and puffiness of the upper and lower eyelids as indexes.

The present invention is an eye form classification map, including a frame axis on which a frame form to be classified based on the comparison with the eye frame form of a standard balanced eye is arranged and a form axis on which an eye form to be classified based on the standard balanced eye form is arranged, and including a graphic chart wherein the both axes being mutually perpendicular are provided and the standard balanced eye form is located at the intersection of the both axes, and an angle form axes are located in respective quadrants sectioned by the frame axis and the form axis.

The present invention is an eye makeup method characterized in that by comparing the standard balanced eye form with the eye form of a subject of makeup, differences in the balance of the both eyes are identified, and eye makeup is applied so as to bring the balance of the eye form of the subject of makeup closer to that of the standard balanced eye. In comparing the standard balanced eye form and that of the subject of makeup, a profile of the eye frame form of the standard balanced eye and the eye frame form of the subject of makeup are superimposed to check size and positions of irises, and, depending on a deviance thereof, the frame forms and angle forms can be evaluated through computer image processing.

The present invention is characterized in that the frame form is the outline shape of the eye contour including the eyelash line of the upper and lower eyelids, the eye form is the three-dimensional shape of the eyelid grooves and the upper and lower eyelids, and the angle form is the angle between a diagonal connecting the inner corner and the outer edge and a horizontal line passing through the inner corner.

The standard balanced eye form is characterized to have the frame form, the proportion of the eye contour vertical dimension to the eye contour horizontal dimension of which is 1:3, the eye form in which there is no conspicuous unevenness in the shape of the upper and lower lids, the curve is fluent from the eyebrow arch bone to the cheekbone, and the one-to-one balance is formed between the eye contour vertical dimension and the width between the upper rim of the eye contour and the eyebrow, and the angle form in which the angle between the diagonal connecting the inner corner and the outer edge and the horizontal line passing through the inner corner is between and equal to 9 degrees and 11 degrees, most preferably 10 degrees. It is also characterized in that the eyelid grooves are intermediate between a double-edged shape and a hidden double edged shape (back eyelid with a fold), and the grooves at the inner corner are narrow and those at the outer edge are wide.

The invention is a cosmetic treatment method characterized in that if the balance of the frame form of a subject of makeup has wider vertical width when compared with the standard balanced eye form, eye makeup is applied to achieve the balance between the vertical width and the horizontal width so that the latter will be three when the former is one, and that if the balance of the frame form of the subject of makeup has wider horizontal width when compared with the standard balanced eye form, the eye makeup is applied by balancing the vertical width and the horizontal width, assuming that a value obtained by trisecting the horizontal width is one.

The method is characterized in that if in the eye form of the subject of makeup, the balance between the width of the eye contour vertical dimension and the width from the upper rim of the eye contour to the eyebrow differs from one to one, the eye makeup is applied so that the balance of the eye form will be one to one, by manipulating how shading in the region between the upper rim of the eye contour and the eyebrow looks.

The invention is characterized in that eye forms are classified, positions on a classification map are determined, and eye makeup, etc. is applied so as to bring an eye of a makeup subject closer to the balance of a standard balanced eye, by extracting a standard balanced eye form onto a sheet object, superimposing the sheet object on a real face of the makeup subject, her facial portrait, etc., relative to size and positions of irises, and determining a deviance from the standard balanced eye form as well as features of the eye frame form, angle form, and eye form of the subject's eye. In addition, it provides the eye form classification or a makeup tool including the transparent sheet object.

According to the present invention, eye forms can be appropriately classified according to the type, by utilizing, as the indexes, the eye frame form, the eye form, the angle form, and a map with an standard balanced eye form centered can be constructed, and an eye form of a particular customer can be positioned on the map, thereby easily and accurately identifying and determining form features of that particular customer. In addition, as any differences from the standard balanced eye form can be easily determined, an eye makeup method for reducing the differences can be identified immediately, thus making it possible to accurately provide a method for bringing the eye closer to the standard balanced eye and making up the eye so that it balances and looks large and attractive, without depending on the empirical rules. The invention can also provide a composite makeup tool that presents an eye form feature analyzing method and a form shaping method by makeup.

BRIEF DESCRIPTION OF THE DRAWINGS

FIG. 10 is a view showing differences between the frame form of the model A and that of the standard balanced eye.

FIG. 12 is a photograph of the model before and after makeup.

BEST MODE FOR CARRYING OUT THE INVENTION

Figure 1:
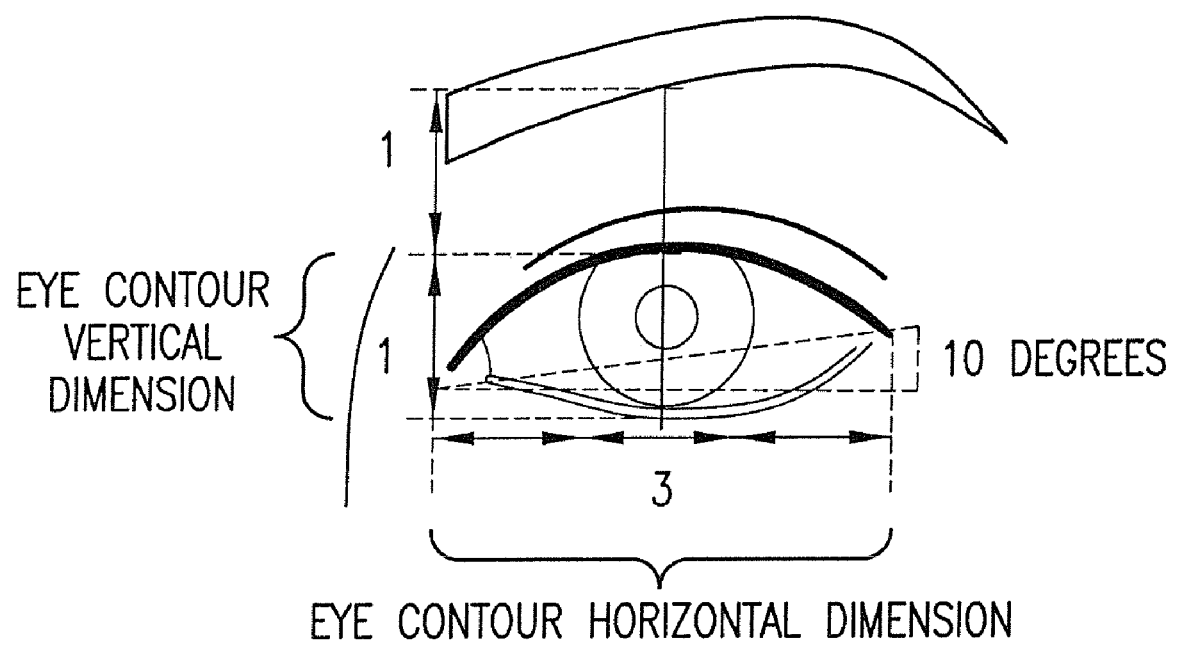
FIG. 1 is a view showing the balance of a standard eye.

In the following, preferred embodiments of the present invention are described. The present invention is characterized in that it enables classification of eye form features by using, as indexes, four elements of a frame axis showing the shape of the eye contour, an eye form axis showing the three-dimensional shape of the eye, an angle axis showing the eye angle form, and a standard balanced eye form. It is also characterized in that it provides a makeup tool that enables form features of a particular person's eye to be easily determined, by placing the classified eye form features on a visually recognizable graphic chart (map) and positioning the eye form of the particular person on the map and thus contributes to makeup of the eye. The invention is further characterized in that it provides an eye makeup method of comparing classified and determined eye form of a subject of makeup with the standard balanced eye form, and making the eye look not only large by bringing the eye form of subject closer to the standard balanced eye form, but also attractive by balancing it.

The frame form is an outline shape of the eye contour defined by the upper and lower eyelids including the eyelash line, and the frame axis is arranged on the axis according to the proportion of the eye contour vertical dimension to the eye contour horizontal proportion. For instance, the frame axis is provided as a vertical axis, wherein the standard balanced eye form, which is to be discussed later, is positioned at the center of the frame, is at the one end of the frame axis, i.e., in the upper side, is positioned an eye form having longer vertical dimension and shorter horizontal dimension than the standard balanced eye that has the proportion of the eye contour vertical dimension to the horizontal dimension of 1:3, and an eye form having shorter vertical dimensions and longer horizontal dimension is positioned at the other end of the axis, i.e., in the lower side.

The eye form showing the three-dimensional shape of the eye is identified by, for instance, an uneven shape of eyelid grooves and puffy upper and lower lids. The form axis is constructed as a horizontal axis being perpendicular to the frame axis, wherein the standard balanced eye form is arranged at the center of the form axis, at one end of the form axis, i.e., to the left, is positioned an eye form wherein puffiness of the upper lid is flatter (a shape of puffy and bulgy eyelids common to single-edged or hidden double-edged eyes) compared with the standard balanced eye form, the lower lid is thin, and a curved surface of a eyeball is not conspicuous, and at the other end of the axis, i.e., to the right, is positioned the eye form wherein puffiness of the upper lid is deep-set (deeply chiseled forms common to double-edged or triple-edged eyes. There is a depression at the orbital border with the eyebrow arch bone, and the bulgy eyeball is conspicuously seen), and the lower lid shows a conspicuous curved surface of the eyeball or is deep-set due to puffy fat in the eye socket.

The eye angle form is the angle between the horizontal line passing through the inner corner of the eye and a diagonal connecting the inner corner and the outer edge, the angle form of the standard balanced eye is between and equal to 9 degrees and 11 degrees, and most probably 10 degrees. Based on this angle form of the standard balanced eye, if the angle is between and equal to 9 degrees and 11 degrees, the eye is determined to be of a standard form. If the angle is smaller than or equal to 9 degrees, the eye is determined to be of a downward slanting form. If the angle is greater than or equal to 11 degrees, the eye is determined to be of upward slanting form. The angle axis showing upward or downward slant is represented as if it individually existed in 4 quadrants sectioned by the two axes when the frame axis and the form axis are projected on a plane.

The form features of the standard balanced eye are as follows: a. the standard balanced eye has the frame form wherein the proportion of the eye contour vertical dimension (a perpendicular line passing through the center of an iris) and the eye contour horizontal dimension is 1:3, b. the shape of the upper and lower eyelids when the face is viewed from the side has no conspicuous unevenness, and the standard balanced eye has the eye form with the fluent curve from the eyebrow arch bone (the slightly-elevated bone lying under the eyebrow area) to the cheekbone, c. the angle between the horizontal line passing through the inner corner of the eye and the straight line connecting the inner corner with the outer edge is 10 degrees, d. the eyelid grooves are intermediate between a double-edged shape and a hidden double-edged shape, and the grooves at the inner corner are narrow and those at the outer edge are wider than the inner corner, and e. the standard balanced eye has the eye form in which the balance of the width of the eye contour vertical dimension and the width from the upper rim of the eye contour to the eyebrow is 1:1. FIG. 1 is a front elevation showing the standard balanced eye form.

Figure 2:
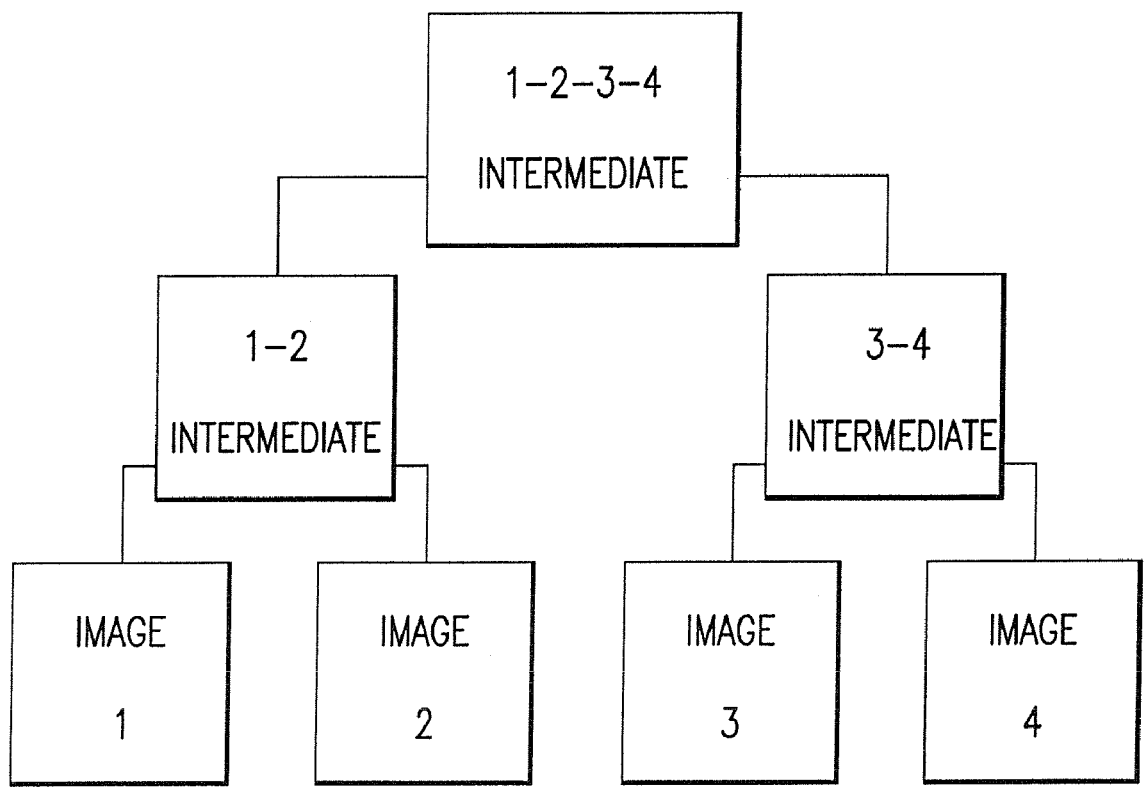
FIG. 2 is a view showing creation of a mean image through repetition of morphing.

Such the form features of the standard balanced eye were created as described below. First, facial portraits of 40 women in 20's were created. Then, applying the image processing technique (morphing) of computer graphics and evenly synthesizing them, we obtained averaged images of the 40 women. Averaging through morphing takes place by specifying corresponding features of 2 facial portraits, and creating the mid-image of shape and colors of the both portraits relative to the features. Then, as shown in FIG. 2, the above steps are repeated for newly created mid-images, and, repetition of morphing will result in a final one image. The final image thus obtained through the image processing represents a mean of the 40 women. The facial portraits of 40 women in 20's were randomly selected without defining any form feature of a face or an eye, and thus there is no bias in their form features.

Such the standard balanced eye form is extracted onto a transparent sheet object such as a film, an acrylic board, glass, etc., and superimposed onto a real face of a makeup subject or her facial portrait, relative to position of the iris. The sheet object can be used as a tool for classifying eye forms, identifying a position on a classification map, or determining a deviance from the standard balanced eye form. A plurality of the transparent sheet objects with different scales shall be prepared, considering size of photographs that might differ depending on size of a face and distance from a shooting camera.

Eyelashes shall be positioned as an element associated with the frame form, because the lash line and density of eyelashes contribute to recognition of a shape of the frame form. In addition, length of eyelashes and the angle form are positioned as elements associated with the eye form, as they contribute to special effects of the eye region. However, the eyelash elements (length and density) are not reflected in classification of the eye type itself, and simply utilized for determining the condition.

Figure 3B:
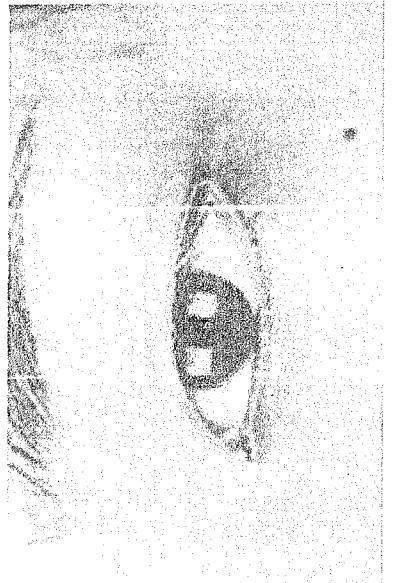
FIG. 3 is a view showing an example for determining a shape of the frame form by computer graphics.
Figure 3A:
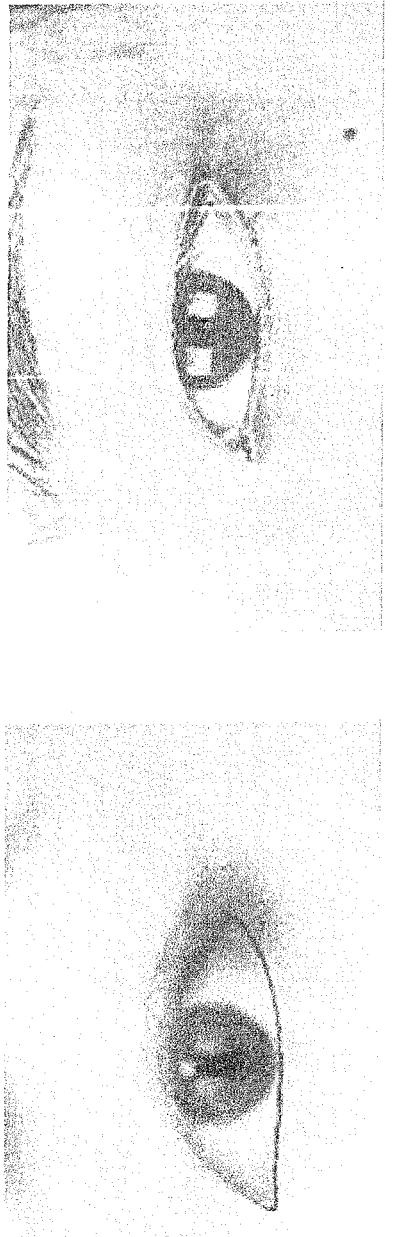
Figure 3C:
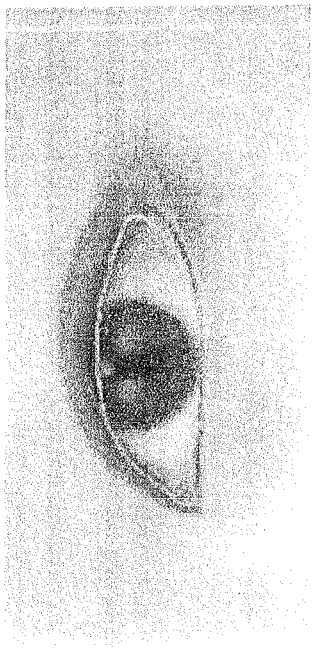

With reference to FIG. 3, a method of evaluating the frame forms and angle forms according to the computer image processing is explained. To evaluate the frame forms and angle forms by the computer image processing, as shown in FIG. 3, the contour of the frame form of the standard balanced eye (A) is superimposed on contour of the frame form of the eye to be compared (B), relative to size and a position of irises of the both eyes. Then, the frame forms and angle forms are evaluated based on a deviance therebetween (C).

Figure 4:
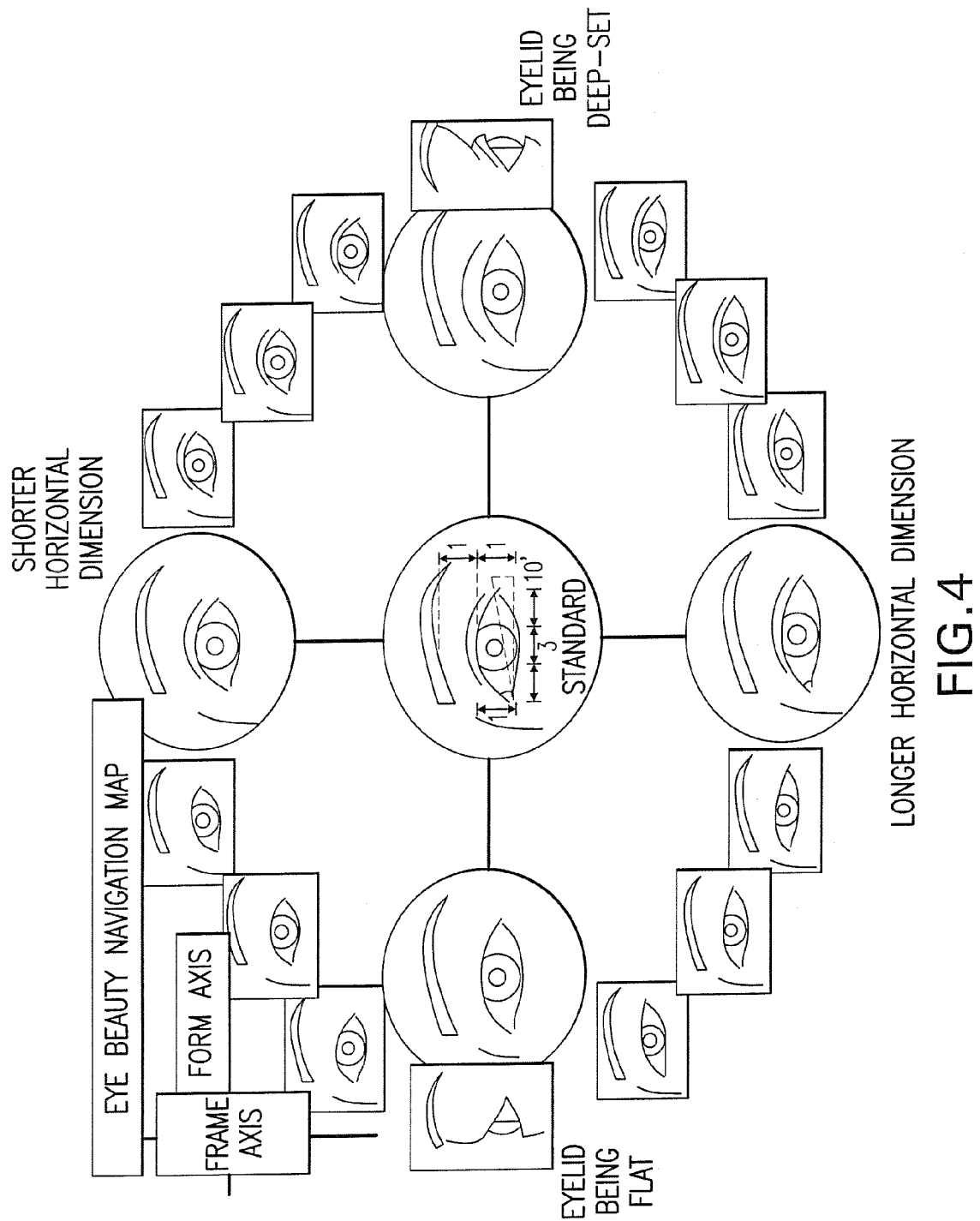
FIG. 4 shows an eye classification map according to the present invention.

As shown in FIG. 4, the eye form classification map is a graphic chart that presents the eye form by using four indexes of the frame axis, eye form axis, angle axis and the standard balanced eye form, placing the standard balanced eye form at the center, which is the intersection point of the frame axis and the form axis, and making the frame axis the vertical axis and the form axis the horizontal axis. On the map are illustrated in respective positions the standard balanced eye form, the eye form with shorter horizontal dimension, the eye form with longer horizontal dimension, as well as the form of the eye having deep-set eyelids and the form of the eye having flat eyelids. The illustration of the standard balanced eye form is positioned at the center of the map, the illustrations of the two frame forms of the eyes with the longer and shorter horizontal dimensions are positioned at the upper and lower ends of the frame form, and the illustrations of the eye forms of the eyes having flat eyelids and deep-set eyelids are positioned at the right and left ends of the form axis. To each illustration are attached the description thereof and the description of the eye form.

As for the eye angle forms, as it is realized that the upward slanting eye form, the standard balanced eye form (with the angle of 10 degrees), the downward slanting eye form exist, respectively, in four quadrants sectioned by the frame axis and form axis when the frame form/eye form are projected onto a plane, the three types of illustrations appear in respective quadrants. The respective illustrations are represented so that the respective eye form features can be easily determined.

Figure 5:
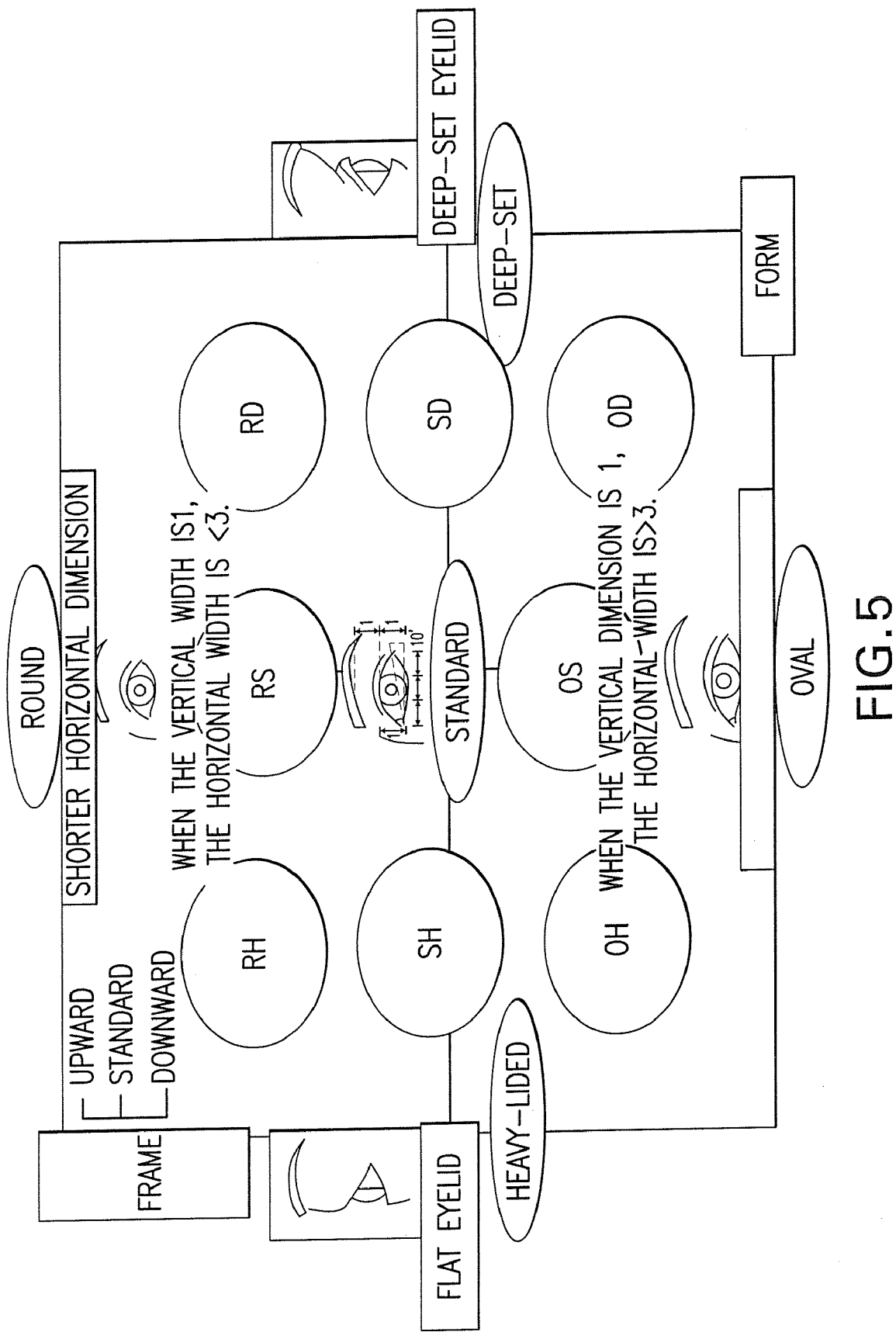
FIG. 5 shows classifications and names of the eye according to the present invention.

FIG. 5 shows the eye form classification types and designations used in the eye form classification map. There are 27 form classification types that have resulted from multiplication of nine major classification types by three minor classification types. In other words, the eye form types are divided into three categories of Round (shorter horizontal dimension), Standard (reference), and Oval (longer horizontal dimension) according to the features of the frame axis, and then into three categories of Heavy-lidded (flat eyelids), Standard (reference), Deep-set (deep-set eyelids). The eye form types positioned in respective quadrants are roughly divided into nine (major classifications), each classification type being represented by a combination of initial letters of the designations of the frame forms and eye forms. In addition, the elements of the angle forms are assessed and sorted into Upward (upward slanting eyes), Standard (reference outer corner), and Downward (downward slanting eyes) (minor classifications). Thus, the eye form types are: nine major classifications times three minor classifications is 27 classifications. In addition, a variety of designations such as Round, Oval, Heavy-lidded, Standard, Deep-set, Upward, Downward, etc., mentioned above, that represent the eye form types are by way of example only, and the invention shall not be limited to such the designations.

In FIG. 5, the eye types of the 27 classifications are indicated only, by using initial letters. For instance, they are RH-S type, SO-D type, etc. The RH-S type represents the eye type having the frame form in which the proportion of the eye contour horizontal dimension to the eye contour vertical dimension is smaller than 3 when the latter is considered 1, i.e., the eye frame has shorter dimension (Round), and the eye form in which the eyelids are flat (Heavy-lidded), yet the angle form is the reference outer corner (Standard) and belongs to the upper left quadrant of FIG. 5. In addition, OS-D type represents the eye type having the frame form in which the proportion of the eye contour horizontal dimension to the eye contour vertical dimension is greater than three when the former is considered one, i.e., it represents the eye type in which the eye frame has longer dimension (Oval), the eye form is standard (Standard), and the angle form is the downward slanting (Downward) type, and is located in the lower central quadrant.

Using the eye classification map of FIG. 5, eye makeup for adjusting the balance according to the eye type can be applied. In other words, in view of the positional relationship between the position of the classified eye type and that of the Standard which is the standard balanced eye form, eye makeup adjusts so as to bring the frame form, the eye form, and the angle form of the eye closer to the form of the Standard. For instance, if the subject eye is of RD-S type, the eye makeup technique for making the horizontal axis look longer is applied in order to bring the frame form having shorter horizontal dimension closer to the standard balance of 1:3. In addition, as the eye form is more deep-set than that of the standard balanced eye, the eye form is adjusted to approximate the eye form of Standard by applying the eye makeup technique for making the eye look flat. In this case, since the angle form is of Standard, no adjustment is needed.

As shown in FIG. 1, since the standard balanced eye form has the proportion between the width of the eye contour vertical dimension and the width from the upper rim of the eye contour to the eyebrow (width of the eyelid) is balanced at 1:1, eye makeup shall be applied in the case that the eye form of the makeup subject is not balanced at 1:1. For instance, a cosmetic treatment method of using brighter colors to reduce a feeling of shading is applied if the eyelids are narrow, while the cosmetic treatment method of using darker colors to emphasize the feeling of shading if the eyelid is wide. Such the makeup techniques apply optical illusion of length or depth to be brought by shading information, and employs the fact that manipulation of the shading information causes different perception to depth and width of a graphic chart.

As described above, if eye makeup is applied to the makeup subject, by comparison with the standard balanced eye form, efforts shall be made to bring differences in the frame forms and eye forms close to those of the standard balanced eye. In this case, it is necessary to compare the eye form of the aforementioned makeup subject with that of the standard balance, and the balance shall be adjusted either vertically or horizontally when eye makeup is applied. Then, if the vertical width is greater than the standard balance of 1:3, makeup is applied by setting the aforementioned vertical width to one so that the horizontal width will be three.

In other words, if either vertical or horizontal dimension of the frame form of the eye of the aforementioned makeup subject is larger, the method uses the larger dimension as a standard. For instance, the vertical width of the frame form of the eye of the aforementioned makeup subject is wider than the standard balance of 1:3, makeup is applied by setting the aforementioned vertical width to one, determining the horizontal width so that it will be three. If the horizontal width is larger, the vertical width will be determined by setting to one the value obtained by trisecting the aforementioned horizontal width, and makeup is applied so that the vertical width will be one. Such the method of determining the balance can enable application of the makeup that can more easily approximate the standard balanced eye form, and can make the eye of the aforementioned makeup subject look large and attractive.

Figure 6:
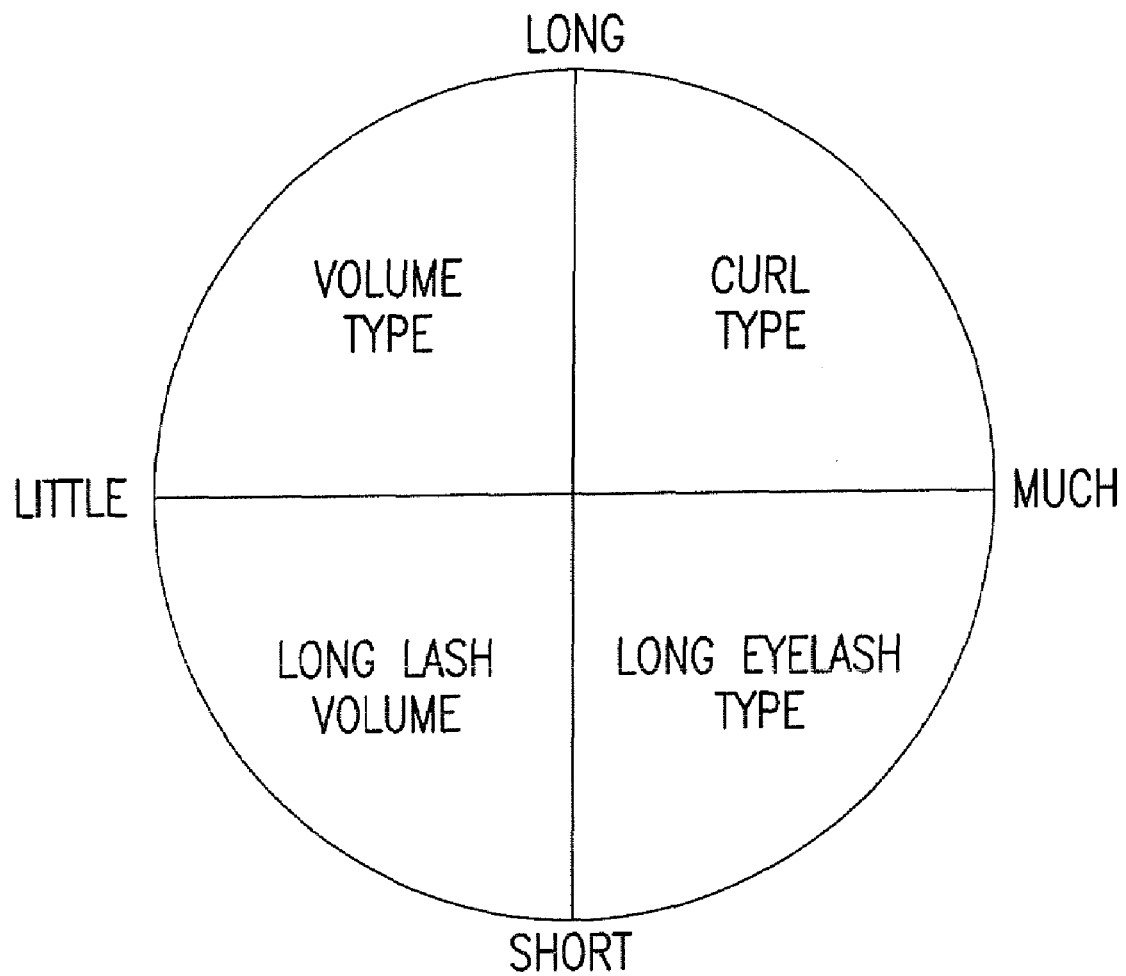
FIG. 6 is a view showing a mascara selection circle.

As use of the eye form classification map of this invention makes it possible to instantly determine a positional relationship between a position of individual eye form and the standard balanced eye form (Standard), and displayed axes present what makeup technique to apply to bring the eye to a target form, makeup can be applied easily. If makeup is also applied to eyelashes, simultaneous use of "Mascara Selection Circle" of FIG. 6 can enable selection of mascara suitable for length and density of the eyelashes. The Mascara Selection Circle is used by positioning its center on the coordinates where the vertical and horizontal axes are mutually perpendicular, and matching the eyelash features of length and density to the eye form features. For instance, if eyelashes are long and dense, they belong to the upper right quadrant, and thus a mascara of curling type may be selected.

Figure 7:
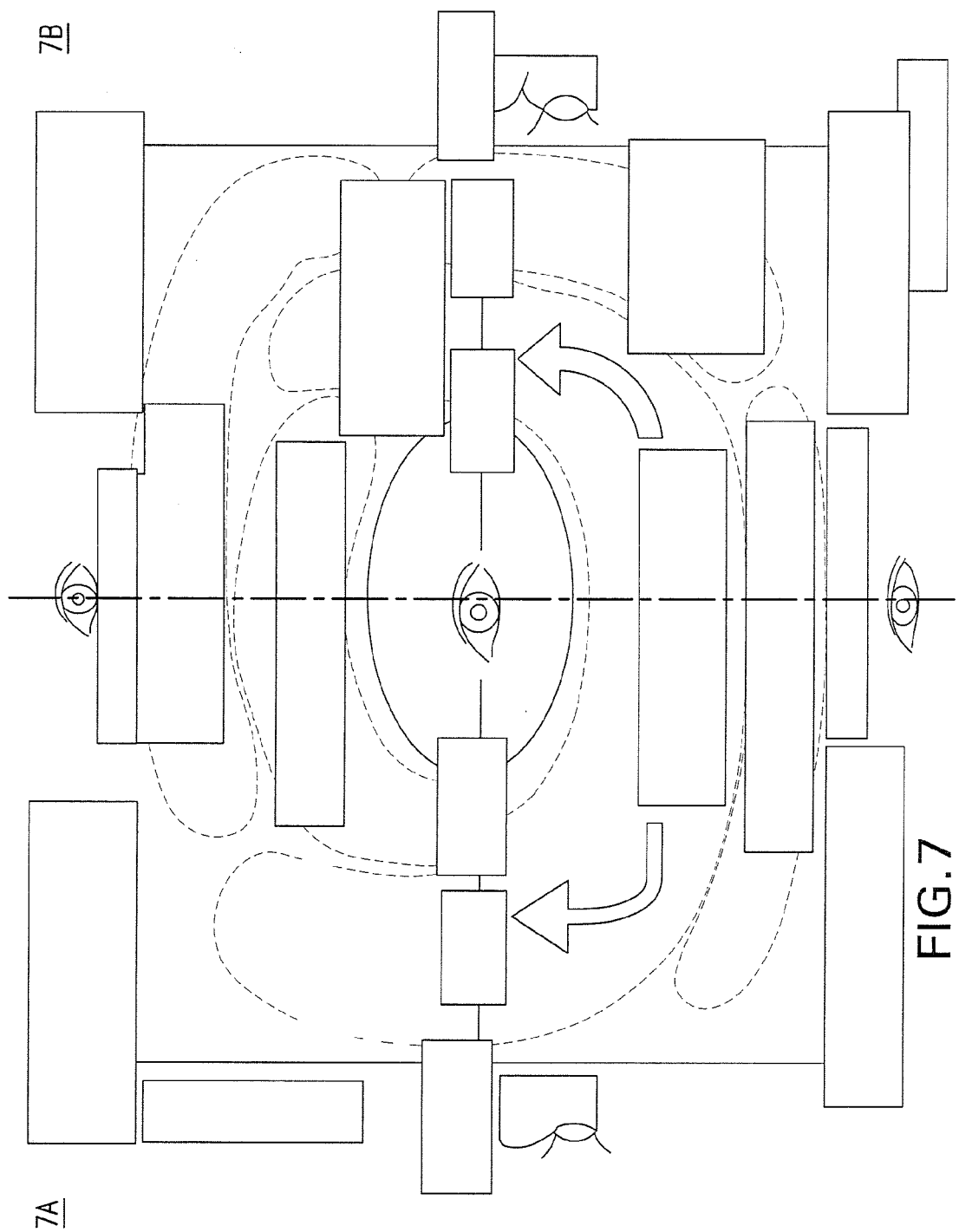
FIG. 7 is a view showing correspondence between the eye form features according to the present invention and general designations.
Figure 7A:
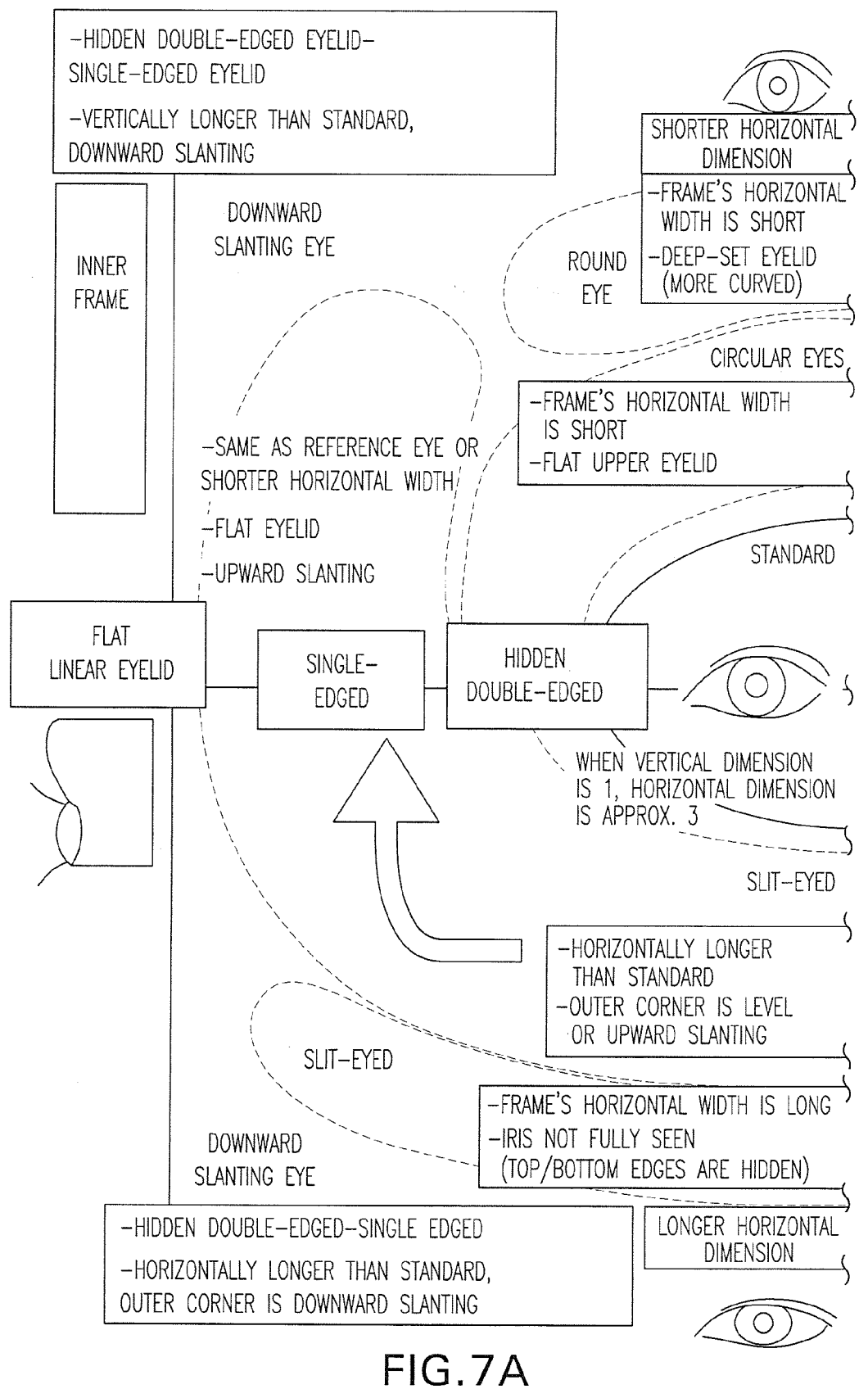
Figure 7B:
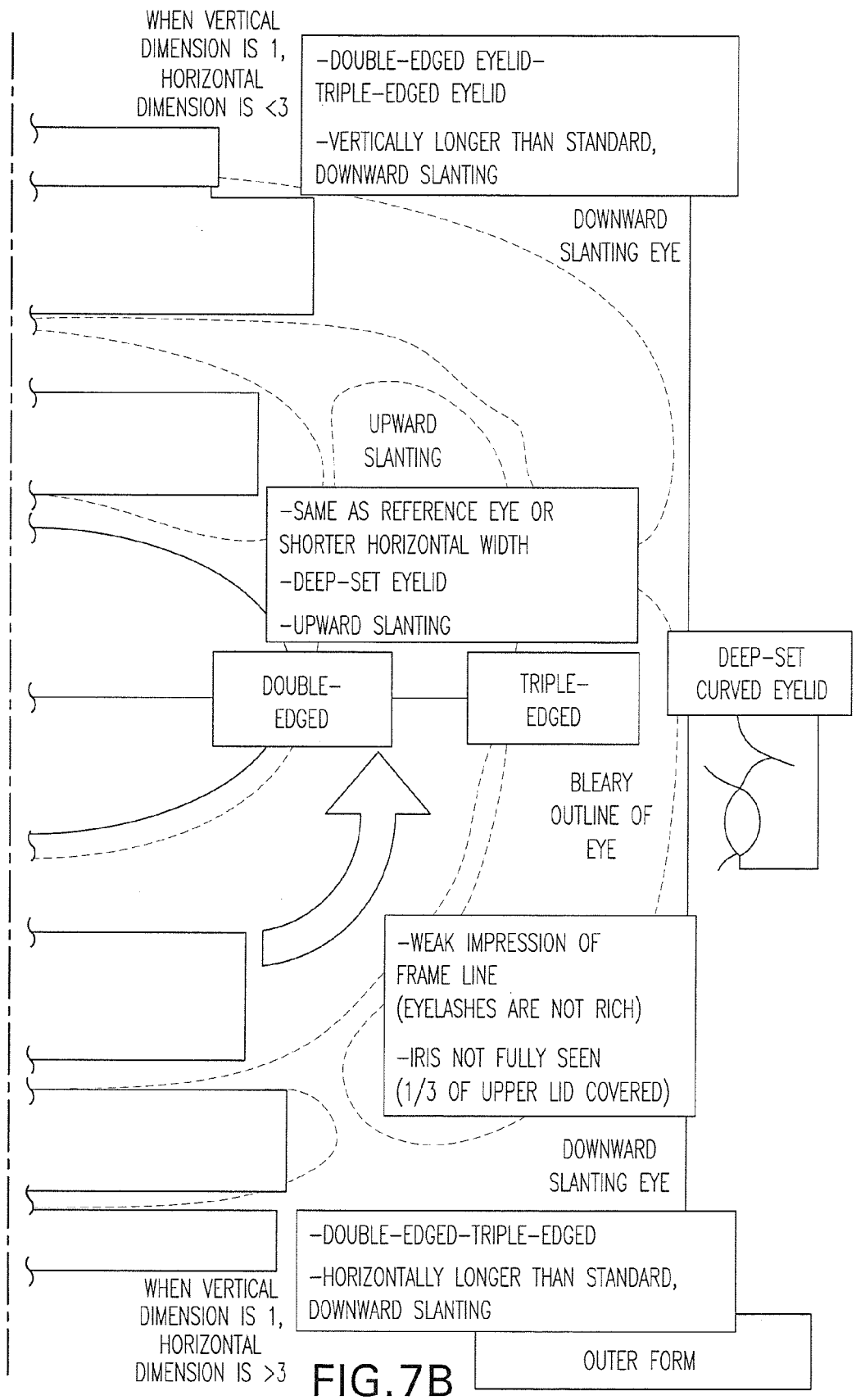

Eyes have such generic designations as round eyes, upward slanting eyes, etc. In accordance with the indexes of the eye form classification map of the present invention, the generic designations can be positioned by the form feature, which could thus enable classification of eye form types according to the generic eye designations that are easier to be understood commonly. FIG. 7 is a map showing correspondence between the eye form features according to this invention and the typical generic designations.

A method of making up the eye so that it looks large, well-balanced and attractive assumes that "the horizontal to vertical ratio of the frame form of the eye be brought close to the ratio of 1:3, and the eye form also be brought close to the depth of the standard balance". Then, in order to verify the assumption, we applied 23 eye makeup patterns to models whose eye form features differ, and, out of them, carefully selected 13 patterns that noticeably exhibit differences of form shaping. Then, using their photographs, we carried out a questionnaire survey.

A method of conducting the survey is as follows: twenty-four women in 20's and 40's, respectively, and 16 beauty technicians working for cosmetic companies were selected as respondents. Using the eye form classification map, we selected nine models from all quadrants, and conducted the survey by using photographs of the models to each of whom we applied each of the 13 patterns of makeup and photographs of the models before wearing the eye makeup. We used the photographs only covering eye regions (front and side) and those of an entire face.

Figure 8:
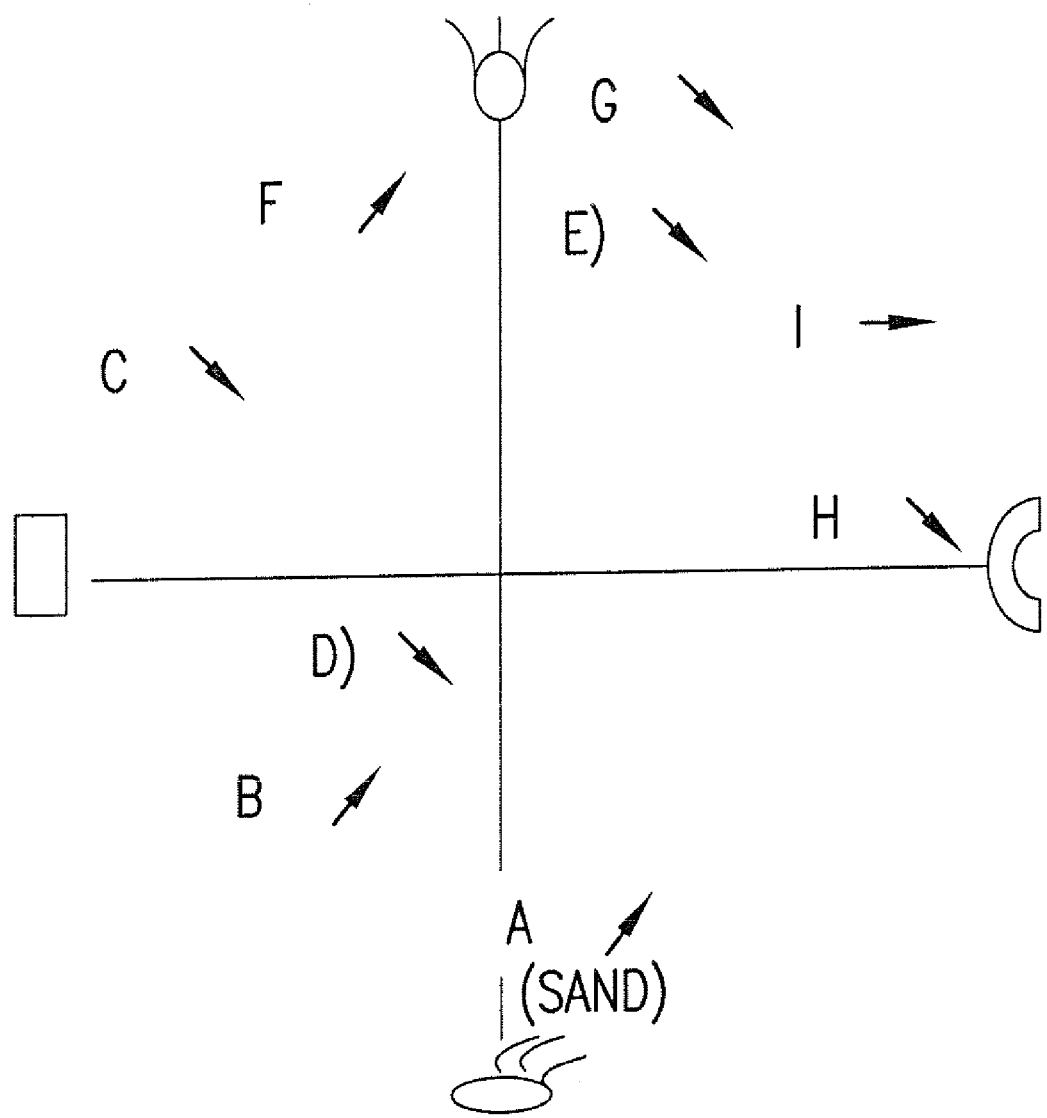
FIG. 8 is a view showing the position on the map of the eye of the model who responded to the questionnaire.
Figure 9B:
FIG. 9 is a view showing examples of eye makeup patterns.
Figure 9D:
Figure 9A:
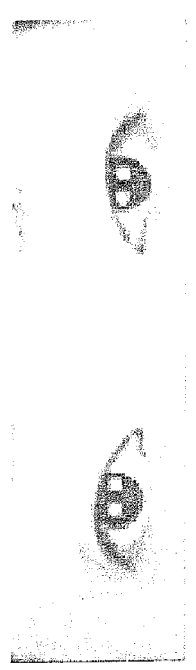
Figure 9C:

The makeup patterns we applied included use of any single item of eyeliner, eye shadows, mascara, and a false eyelash or use of a combination thereof. We also provided a total of 13 eye makeup patterns with variations of makeup techniques such as sharply lining with the eyeliner or placing eye shadow, smudging them away, or adding mascara commonly or heavily. FIG. 8 shows positions on the map of the eyes of nine models, with alphabet letters corresponding to respective models, and arrows indicating the eye angle forms.

FIG. 9 shows examples of the makeup patterns, the upper left photograph (A) shows the eyes prior to makeup, the upper right photograph (B) shows the eyes with only lots of mascara added on the upper and lower lashes, the lower left photograph (C) shows the makeup not only highlighting the lash line with black eye line and outlining the frame form but also smudging away the upper line of the frame form, and the lower right photograph (D) shows the makeup in which the rims are lined and then smudged away, eye shadows are placed on the upper lids to give added depth, and false eyelashes are added on the upper lids.

In response to the survey item, the respondents are asked to pick three photographs of eye regions for three items, namely, liking disliking or looking large, in the corresponding order. The respondents are also asked to choose one photograph each for three items, namely, the eye makeup is adapted to model's eyes, it fits and looks large, and the makeup is best. In addition, for facial portraits, they are asked to select one photograph each of the four items, namely, the eyes look largest, the makeup fits and the eyes look large, the respondent likes the photograph, or does not like it.

As a result of the questionnaire survey, it was found that the makeup pattern of the 3 models whose photographs of the eyes were evaluated as "the makeup fits on her and her eyes look large" was achieved by the makeup techniques that (i) the upper and lower rims were lined with the eyeliner and the eye shadow was placed on the upper and lower lids so as to approximate the frame form balance of 1:3, (ii) the eye shadow was smudged away to bring the depth of the eyelids close to the standard balance, (iii) loads of mascara were added on the eyelashes on which the false eyelashes were applied, thus highlighting the eyelashes, setting the horizontal to vertical ratio of the length of the eye regions including lashes to the balance of 1:3 which means only the frame form is large, and finalizing the balance of the eye form so that the proportion between the eye contour vertical dimension and size of the eyelids looks 1:1.

It was observed that there was some variation in tolerance to degree of makeup (thickness) depending on models' inherent eye features, for instance, models who have long eyelashes by nature pass intentionally false eyelashes. However, for other models, the makeup pattern determined as fitting and making the eyes look large had commonality that the ratio of the frame form was brought close to 1:3 and the proportion of the eye form was brought close to the standard balance of 1:1. The above findings revealed that even for the eyes with the form features in all quadrants of the eye classification map, bringing the ratio of the frame form close to 1:3 and that of the eye form close to the standard balance of 1:1 had the effect of making the eyes look "fitting and large".

Hence, it was made known that the eye makeup method of making the eyes "fitting and large" could be realized in any eye type, by following the principle of adjusting it to the balance of a "standard balanced eye form" that serves as a standard of the classification map. This enabled creation of a makeup tool that simultaneously presents an eye form classification method which is accurate and easy, and the eye makeup principle for making individual classified eyes look large and attractive.

Examples

In the following, according to the eye form classification method of the present invention, we describe in detail the process of classifying a customer's eye, applying it onto the map, and applying necessary makeup to it so that the eye looks large and attractive. To be specific, we applied eye makeup to a customer who visited our salon, with the following steps 1 to 4.

(step 1: Identification of type and position of an eye) Using Eye Beauty Navigation Map in FIG. 5, we determine an eye type of each customer by matching it against a standard balance. Now, we take model A as an example. (i) When we line the contour of the frame form of the eye of model A and compare it with the contour of "the standard balanced eye", we know that the vertical width of the former is shorter and the horizontal width is longer. Then, we can determine that the frame axis lies in the lower area, i.e., type O. (ii) As the eyelid is single-edged and flatter, we determine that the form axis lies in the left area, i.e., type H. (iii) Lastly, in terms of the angle form of the outer edge, as it slants more upward than the standard balance, it is type U. Thus, the eye type of model A is OH-U.

FIG. 10 represents the frame form of model A (FIG. 10A) in fine solid line (FIG. 10B), shows the frame forms of the standard balance eye in solid line, the frame form of the standard balanced eye in thick solid line (FIG. 10C). Then, we can easily determine differences in the frame form of the standard balance and the frame form of model A, by superimposing the both frame forms, as shown in FIG. 10C. Such the determination can be simply done by graphic processing of the computer, and combining it with the map shown in FIG. 5 may enable direct output of the eye classification type of model A.

(step 2: Checking a customer's degree of makeup and requests) Depending on preference of a customer, the degree of makeup to be applied to the eye can be determined. The eye makeup method according to the present invention may be implemented without using all eye makeup items, when the frame form and the eye form are adjusted. For instance, the eye frame form can be lined by the eyeliner only or by using both of the eyeliner and eye shadows. To sum up, it is imperative to shape the eye forms according to the principle, and then there is no special limit by the makeup items. Thus, according to the customer's preference, the invention can deal with the varying degree of makeup ranging from natural makeup to thick makeup. As the model A has strong interest in makeup and wishes to wear firm makeup, we decided to use the makeup items such as the eyeliner pencil, eye shadows, and mascara.

Figure 11:
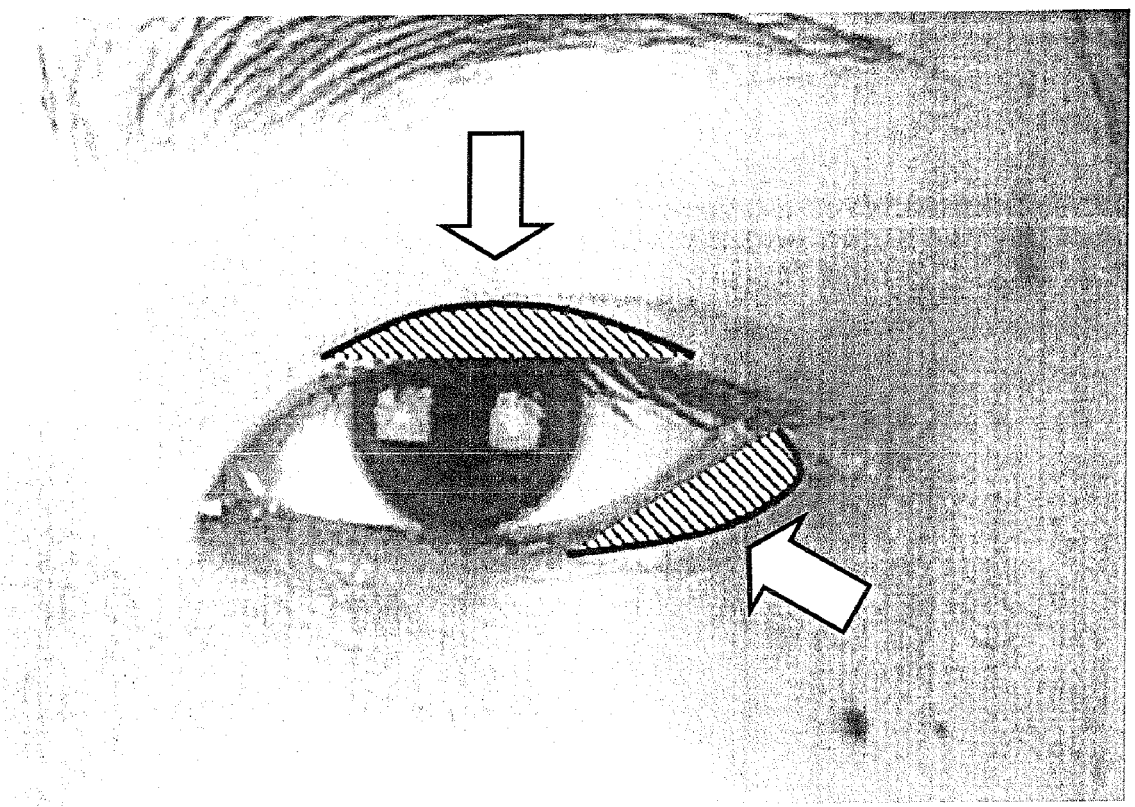
FIG. 11 is a view showing differences of the model A and the standard balanced eye.

(step 3: Checking any difference between a position of the eye on the map and the balance of the standard balanced eye, and determining direction of the makeup) A deviation in the frame forms of the model A and of the standard balanced eye constitutes a shaded area as shown in FIG. 11. Thus, we adopted the makeup policy of (i) extending the vertical width of the eye region over the upper lid, (ii) adjusting an upward slant of the outer corner, and (iii) making no modification to the horizontal width as it is almost same.

(step 4: Application of eye makeup) First, eye makeup is applied by using the makeup items to be decided by preference of the model A as set forth in step 2. In the case of the model A, she has strong interest in makeup and intends to use false eyelashes, we use the eyeliner pencil, eye shadows, and mascara to apply a firm degree of makeup. To be specific, we apply the makeup policy of (i) extending the vertical width of the eye region over the upper lid, (ii) reverting the upward slant of the outer edge to the standard level, and (iii) making no modification to the horizontal width as it is almost same as the standard balance.

To implement the policy (i), we apply the eyeliner pencil to the upper line of the frame form to improve it, and line the lash line so as to fill interspaces. The line should be slightly thicker in the center to bring the curved line of the upper frame form closer to the shaded area (the standard balanced eye). Then, using the eye shadow, we modify the eye form. Using the upper shaded area as a guide, we place shadow and smudge it outwardly, add feeling of shading to the upper lid, thereby making rather puffy eyelid look slightly deepened. We can give added depth by using shady shadow of darker tone.

To implement the policy (ii) of bringing the upper slant of the outer edge close to the standard level, we apply makeup by emphasizing the hatched area under the outer corner. First, we extend eyeliner on the lower lash line to fill interspaces. Then, lining the outer corner slightly downward could alleviate the upward slant of the outer edge. Place shadow on the hatched area, so that the eye frame form approximate the ratio of 1:3 of the standard balance. With this we can modify the ratio and shape of the frame form as well as the angle form.

(iii) Since we make no modification to the horizontal width as it is almost same as the standard balance, we should not extend or narrow the horizontal width when making modifications of (i) and (ii) above. In fact, we may extend eyeliner or place shadow, following the horizontal width of the subject's eye.

In addition, when making up eyelashes, we should select the most appropriate mascara by using the mascara selection tool. Since eyelashes of the model A are long and not many, we select mascara of volume type by turning the selection circle so that the relevant part (long/little) of the circle can be at the position of the eye form type OH. In addition, the mascara selection circle shall be a transparent or translucent sheet object, and is preferably configured so that it is rotatably coupled to the map by grommet fittings, etc. and can be turned 360 degrees. In practice, we use the mascara selection circle by placing the sheet showing the mascara selection circle at the center of the map, rotatably joining it and setting the relevant position of the eyelash type to the position of the classified eye type.

To modify eyelashes and apply mascara, we first curl upper lashes upward with an eyelash curler. Since the model A has long lashes, the vertical width will be too much and break down the frame form balance, if we curl them upward too much. Thus, we lift up eyelashes at the inner and outer corners and not curl lashes in the central part too much. When applying mascara, similar to the above, add it lightly at the center and apply it heavily at the inner and outer edges to give lashes more body. The above steps end adjustment of the ratio of the frame form and the depth of the eye form, and modification of eyelashes related to both the frame form and eye form, and could approximate the standard balanced eye form. FIG. 12 shows photographs of the eyes and entire face before and after the makeup.

We prepare a tool having the standard balanced eye form shown in FIG. 1 represented on a transparent sheet object. Although FIG. 1 shows the proportion of the eye contour vertical dimension, that of the eye contour horizontal dimension and the angle, we can do without such the indication. The transparent sheet object to use may be a film, a plastic sheet such as acryl, etc., or a glass sheet, etc. The representation may be formed by printing, photographic printing, copying, and other means. By superimposing the transparent sheet object having the standard balanced eye form represented on a real face of a makeup subject or her photograph, relative to size and position of the iris, we can determine any differences or deviance from the standard balanced eye form, and use the sheet to classify the eye form of the relevant subject, determine the position on the classification map, and apply the eye makeup.

It is preferable to prepare a plurality of the transparent sheet objects having different scales, thus being able to handle photographs differing depending on face size, a distance from a shooting camera, etc. As we can match the size and position of the iris by making the sheet contact or separate when comparing with a real face of the subject, we do not necessarily have to prepare a plurality of patterns having different scales. The transparent sheet object may be prepared as a makeup tool, kept at a salon so that makeup instructors or customers can use it, or sold so that customers can use it at home.

The invention claimed is:

1. An eye form classification map for use in the application of eye makeup, comprising a graphic sheet upon which a standard balanced eye form is located at an intersection of horizontal axis and vertical axis,
    wherein a ratio of an eye contour vertical dimension to an eye contour horizontal dimension of the standard balanced eye form is 1 to 3, a ratio of the width of the eye contour vertical dimension to a width from an upper rim of the eye contour to an eye brow of the standard balanced eye form is 1 to 1, and an angle between a diagonal line connecting an inner corner with an outer edge and a horizontal line passing through the inner corner of the standard balanced eye form is greater than or equal to 9 degrees and less than or equal to 11 degrees,
    wherein on the vertical axis, eye forms are classified based on whether the ratio of the eye contour vertical dimension to the eye contour horizontal dimension is higher or lower than 3 when the vertical dimension is 1, and
    wherein on the horizontal axis, the eye forms are classified based on whether eyelid is heavy-lidded (flat eyelids) or deep-set (deep-set eyelids).

2. The eye form classification map for use in application of eye makeup according to claim 1, wherein in four quadrants sectioned by the vertical axis and the horizontal axis, the eye forms are classified based on whether an angle between a diagonal line connecting the inner corner with the outer edge and the horizontal line passing through the inner corner of the eye form is less than 9 degrees or greater than 11 degrees.

\* \* \* \* \*